(12) United States Patent
Power (10) Patent No.: US 10,092,165 B2
(45) Date of Patent: Oct. 9, 2018

(54) SYSTEM AND METHOD FOR ENHANCING PICTURE-IN-PICTURE DISPLAY FOR IMAGING DEVICES USED FOR SURGICAL PROCEDURES (71) Applicant: Covidien LP, Mansfield, MA (US)

(72) Inventor: James M. Power, Shanghai (CN)

(73) Assignee: Covidien LP, Mansfield, MA (US)

( * ) Notice: Subject to any disclaimer, the term of this patent is extended or adjusted under 35 U.S.C. 154(b) by 400 days.

(21) Appl. No.: 14/777,785

(22) PCT Filed: Mar. 19, 2014

(86) PCT No.: PCT/US2014/031197
§ 371 (c)(1),
(2) Date: Sep. 17, 2015

(87) PCT Pub. No.: WO2014/153396
PCT Pub. Date: Sep. 25, 2014

(65) Prior Publication Data
US 2016/0278611 A1 Sep. 29, 2016

Related U.S. Application Data (60) Provisional application No. 61/803,498, filed on Mar. 20, 2013.

(51) Int. Cl.
*H04N 7/18* (2006.01)
*A61B 1/00* (2006.01)
(Continued)

(52) U.S. Cl.
CPC ........ *A61B 1/0005* (2013.01); *A61B 1/00006* (2013.01); *A61B 1/00193* (2013.01);
(Continued)

(58) Field of Classification Search
CPC .............. A61B 1/0005; A61B 1/00006; A61B 1/00193; A61B 1/04; A61B 1/3132;
(Continued)

(56) References Cited

U.S. PATENT DOCUMENTS 7,066,928 B2   6/2006   Dick et al.
8,155,479 B2   4/2012   Hoffman et al.
(Continued)

FOREIGN PATENT DOCUMENTS

EP          1921547 A2    5/2008
EP          2149331 A1    2/2010
WO       WO 1993/06768   4/1993

OTHER PUBLICATIONS

European Search Report dated Jan. 17, 2017, issued in EP Application No. 14767799.
(Continued)

*Primary Examiner* — Mohammed Rahaman
*Assistant Examiner* — Richard Carter (57) ABSTRACT A system for controlling a display of image data is presented including a first imaging unit for capturing a first set of images and a second imaging unit for capturing a second set of images. The system also includes a display unit configured to display the image data in a picture-in-picture mode, such that the display unit displays the first set of images in a first panel having a first size and the second set of images in a second panel having a second size, where the first size is greater than the second size.

18 Claims, 8 Drawing Sheets (51) Int. Cl.
    *A61B 17/34*     (2006.01)
    *A61B 1/04*     (2006.01)
    *G06F 3/0481*     (2013.01)
    *G06F 3/0484*     (2013.01)
    *G06F 3/0488*     (2013.01)
    *H04N 5/232*     (2006.01)
    *A61B 1/313*     (2006.01)
    *A61B 90/00*     (2016.01)
    *A61B 34/20*     (2016.01)
    *A61B 34/00*     (2016.01)

(52) U.S. Cl.
    CPC .............. *A61B 1/04* (2013.01); *A61B 1/3132* (2013.01); *A61B 17/3423* (2013.01); *G06F 3/04817* (2013.01); *G06F 3/04847* (2013.01); *G06F 3/04886* (2013.01); *H04N 5/23216* (2013.01); *H04N 5/23293* (2013.01); *A61B 1/313* (2013.01); *A61B 34/20* (2016.02); *A61B 34/25* (2016.02); *A61B 2017/3429* (2013.01); *A61B 2090/3612* (2016.02); *A61B 2090/371* (2016.02)

(58) Field of Classification Search
    CPC ..... A61B 17/3423; A61B 34/20; A61B 34/25; A61B 2090/3612; A61B 2090/371; G06F 3/04817; G06F 3/04847; G06F 3/04886; H04N 5/23216; H04N 5/23293
    USPC ............. 348/65, 79, 333.11, 14.12; 600/201; 434/262; 386/248
    See application file for complete search history.

(56) References Cited

U.S. PATENT DOCUMENTS

| | | | |
|---|---|---|---|
| 8,189,993 B2* | 5/2012 | Tashiro | H04N 5/76 386/248 |
| 8,398,541 B2 | 3/2013 | DiMaio et al. | |
| 8,808,164 B2 | 8/2014 | Hoffman et al. | |
| 2007/0021738 A1 | 1/2007 | Hasser et al. | |
| 2007/0238081 A1* | 10/2007 | Koh | G09B 23/285 434/262 |
| 2009/0192524 A1 | 7/2009 | Itkowitz et al. | |
| 2010/0063355 A1 | 3/2010 | Matuura | |
| 2010/0245557 A1* | 9/2010 | Luley, III | G02B 21/0012 348/79 |
| 2011/0249086 A1* | 10/2011 | Guo | H04N 7/147 348/14.12 |
| 2012/0108955 A1* | 5/2012 | Razzaque | A61B 1/0005 600/424 |
| 2012/0209123 A1 | 8/2012 | King | |
| 2012/0289782 A1 | 11/2012 | Viola | |
| 2013/0314580 A1* | 11/2013 | Ju | H04N 5/23222 348/333.11 |
| 2014/0005484 A1* | 1/2014 | Charles | A61B 17/02 600/201 |

OTHER PUBLICATIONS

International Search Report for (PCT/US2014/031197) date of completion is Aug. 13, 2014 (3 pages).

\* cited by examiner

SYSTEM AND METHOD FOR ENHANCING PICTURE-IN-PICTURE DISPLAY FOR IMAGING DEVICES USED FOR SURGICAL PROCEDURES

CROSS-REFERENCE TO RELATED APPLICATIONS

This application is a U.S. National Stage Application filed under 35 U.S.C. § 371(a) of International Patent Application No. PCT/US2014/031197, filed Mar. 19, 2014, which claimed benefit of, and priority to, U.S. Provisional Patent Application 61/803,498, filed on Mar. 20, 2013. The entire contents of each of the above applications is hereby incorporated by reference.

BACKGROUND

Technical Field

The present disclosure relates to endoscopic image output systems. More particularly, the present disclosure relates to systems and methods for enhancing picture-in-picture displays in imaging devices for providing a surgeon with improved endoscopic viewing and orientation capabilities.

Background of Related Art

Endoscopy refers to techniques used to inspect or to look into internal cavities or hollow structures. Endoscopic surgery, also called minimal access surgery, has become widely accepted because of clear-cut advantages such as a decreased postoperative morbidity, less pain, and a shorter hospitalization. Endoscopic surgery, however, is technically more demanding than 'classical open surgery' for several reasons such as smaller instruments, the limitation of the smaller entry ports, and limited visibility of the area operated upon.

Moreover, endoscopy involves image guided surgical navigation, which is the process of planning minimally invasive surgical approaches and guiding surgical tools towards targets inside a patient's body with the help of anatomical imaging information obtained with techniques such as ultrasound, magnetic resonance, and various radiographic techniques. Such anatomical imaging information is useful because during a minimally invasive procedure, the surgical tools and the subcutaneous anatomy are not directly visible to the surgeon. The combination of endoscopy and image guided surgery is interesting because it brings together the interior view of the endoscope and the exterior perspective of the image guided surgical system.

The value of using an image guidance system in conjunction with variable direction of view endoscopy is potentially much greater than for standard fixed-angle endoscopy. However, a problem introduced by variable direction of view endoscopes is that it is difficult for the surgeon to estimate the changing endoscopic line of sight, which has a variable relationship to the shaft axis, because the tip of the instrument is concealed during use. Acquiring an external estimate of where the endoscope is "looking" during a procedure is important as the surgeon tries to integrate preexisting knowledge of the anatomy with the viewing process.

Therefore, it should become apparent that there is a need for a method which provides at least the following capabilities: improved endoscopic viewing and orientation capabilities, global monitoring of endoscopic position and viewing direction, and improved surgical approach and procedure planning SUMMARY Accordingly, an image output system for controlling displaying of data is provided. The system includes a first imaging unit for capturing a first set of images and a second imaging unit for capturing a second set of images. The system also includes a display unit configured to display the image data in a picture-in-picture mode, such that the display unit displays the first set of images in a first panel having a first size and the second set of images in a second panel having a second size, where the first size is greater than the second size.

In further embodiments, the display unit is a touchscreen display unit configured to include a set of virtual icons including panning control icons, zooming control icons, rotating control icons, and freeze control icons.

In yet another embodiment, the display unit includes a storage medium for storing the first and second set of images captured by the first and second imaging units. The storage medium may be optical or magnetic.

The picture-in-picture mode allows for at least a dual image panel, a triple image panel, and a quad image panel. Additionally, a size of the first set of images and a size of the second set of images is permitted to be adjusted in real-time. Also, a position of the first set of images and a position of the second set of images is permitted to be adjusted in real-time.

In yet another embodiment, each of the first and second panels includes a lighting icon for separately controlling at least intensity and color of the first and second set of images captured.

Moreover, the first panel is selectively interchanged with the second panel, and vice versa. Alternatively, each of the first and second panels include a horizontal and vertical processing function for selectively performing horizontal and vertical enlargement or reduction of the first and second set of images captured.

In yet another exemplary embodiment, the first imaging unit includes a first sensing unit and the second imaging unit includes a second sensing unit, such that the first and second sensing units automatically detect each others presence and orientation within a body cavity.

The display unit may further include, in certain exemplary embodiments, a motion detection unit so that a size and position of the first and second panels is adjusted based on a user's hand or finger motion commands detected by the motion detection unit.

Also, an image output system for displaying image data is provided. The system includes a support structure including a plurality of ports for facilitating introduction of a plurality of surgical instruments therethrough. The system also includes a plurality of imaging units mounted on the plurality of surgical instruments for capturing a plurality of images. The system further includes a display unit for displaying one or more picture-in-picture configurations of the plurality of images captured by the plurality of imaging units, the picture-in-picture configurations configured to display the plurality of images within a plurality of panels.

Additionally, a method of displaying image data is provided. The method includes the steps of capturing a first set of images via a first imaging unit and capturing a second set of images via a second imaging unit. The method also includes the step of displaying the image data in a picture-in-picture mode, via a display unit configured to display the first set of images in a first panel having a first size and the second set of images in a second panel having a second size, where the first size is greater than the second size.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

The following detailed description illustrates the present disclosure by way of example, not by way of limitation of the principles of the present disclosure. This description will clearly enable one skilled in the art to make and use the present disclosure, and describes several embodiments, adaptations, variations, alternatives and uses of the present disclosure, including what is presently believed to be the best mode of carrying out the present disclosure.

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user.

Figure 1:
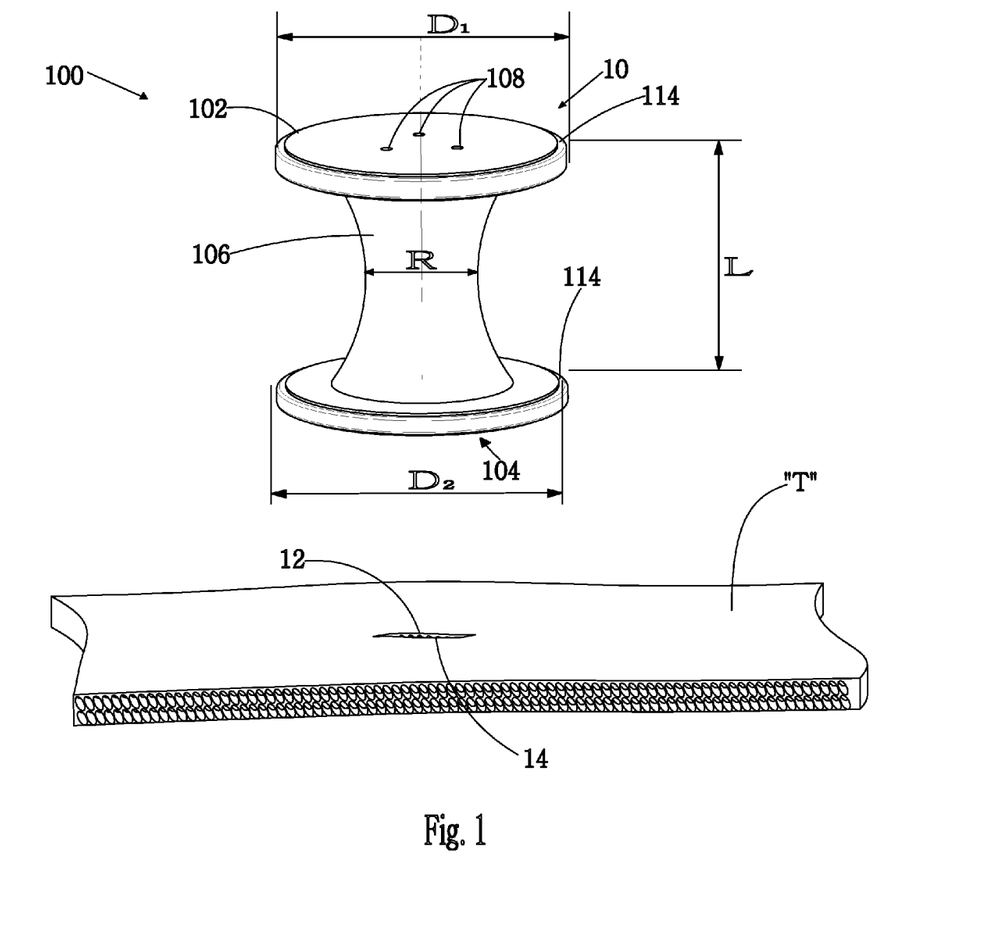
FIG. 1 is a front perspective view of a surgical apparatus in accordance with the present disclosure shown in an expanded condition illustrating a seal anchor member positioned relative to the tissue.
Figure 2:
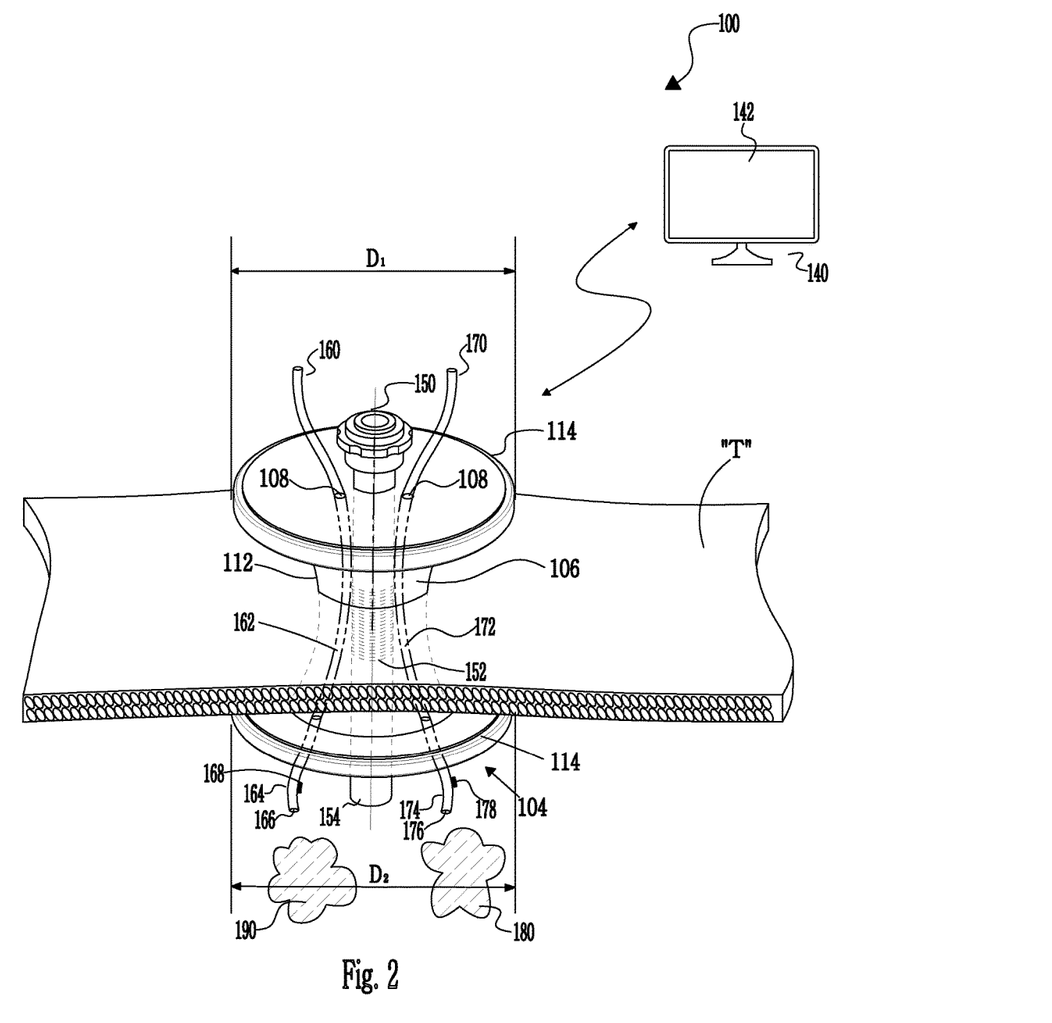
FIG. 2 is a front perspective view of the seal anchor member shown in the expanded condition and subsequent to its insertion into the incision, the seal anchor member having a plurality of surgical instruments inserted therethrough, the plurality of surgical instruments communicating with a display unit having a display screen, in accordance with the present disclosure.

Referring to FIGS. 1-2, a surgical apparatus 10 for use in a surgical procedure, e.g., a minimally invasive procedure is illustrated. Surgical apparatus 10 includes seal anchor member 100 (or access assembly or access port) having respective trailing (or proximal) and leading (or distal) ends 102, 104 and an intermediate portion 106 disposed between the trailing and leading ends 102, 104. Seal anchor member 100 includes one or more ports 108 that extend longitudinally between trailing and leading ends 102, 104, respectively, and through seal anchor member 100.

Seal anchor member 100 is preferably formed from a suitable foam material having sufficient compliance to form a seal about one or more surgical objects, and also establish a sealing relation with the tissue, "T."

Proximal end 102 of seal anchor member 100 defines a first diameter $D_1$ and distal end 104 defines a second diameter $D_2$. In one embodiment of seal anchor member 100, the respective first and second diameters $D_1$, $D_2$ of the proximal and distal ends 102, 104 are substantially equivalent, as seen in FIG. 1, although an embodiment of seal anchor member 100 in which diameters $D_1$, $D_2$ are different is also within the scope of the present disclosure. As depicted in FIG. 1, proximal and distal ends 102, 104 define substantially planar surfaces. However, embodiments are also contemplated herein in which either or both of proximal and distal ends 102, 104, respectively, define surfaces that are substantially arcuate (i.e., top and bottom surfaces are substantially concave) to assist in the insertion of seal anchor member 100 within a tissue tract 12 defined by tissue surfaces 14 and formed in tissue "T," e.g., an incision.

Intermediate portion 106 defines a radial dimension "R" and extends longitudinally between proximal and distal ends 102, 104, respectively, to define an axial dimension or length "L." The radial dimension "R" of intermediate portion 106 varies along the axial dimension, or length, "L" thereof. Accordingly, seal anchor member 100 defines a cross-sectional dimension that varies along its length "L," which facilitates the anchoring of seal anchor member 100 within tissue "T." However, an embodiment of seal anchor member 100 in which the radial dimension "R" remains substantially uniform along the axial dimension "L" thereof is also within the scope of the present disclosure.

The radial dimension "R" of intermediate portion 106 is appreciably less than the respective diameters $D_1$, $D_2$ of proximal and distal ends 102, 104 such that seal anchor member 100 defines an "hour-glass" shape or configuration to assist in anchoring seal anchor member 100 within tissue "T." However, in an alternate embodiment, the radial dimension "R" of intermediate portion 106 may be substantially equivalent to the respective diameters $D_1$, $D_2$ of proximal and distal ends 102, 104. In cross section, intermediate portion 106 may exhibit any suitable configuration, e.g., substantially circular, oval or oblong.

Referring to FIGS. 1-2, seal anchor member 100 is adapted to transition from an expanded condition to a compressed condition so as to facilitate the insertion and securement thereof within tissue tract 12 in tissue "T." In the expanded condition, seal anchor member 100 is at rest and the respective radial dimensions $D_1$, $D_2$ of the proximal and distal ends 102, 104 of seal anchor member 100, as well as the radial dimension R of the intermediate portion 106 are such that the seal anchor member 100 cannot be inserted within tissue tract 12. However, in the compressed condition, proximal and distal ends 102, 104 of seal anchor member 100, as well as intermediate portion 106 are dimensioned for insertion into tissue tract 12.

An external force may be applied to seal anchor member 100 to cause the seal anchor member 100 to assume the compressed condition. The external force may be directed inwardly and when seal anchor member 100 is subjected thereto, e.g., when seal anchor member 100 is squeezed, seal anchor member 100 undergoes an appreciable measure of deformation, thereby transitioning into the compressed condition.

Referring back to FIG. 1, one or more positioning members 114 may be associated with either or both of trailing (or proximal) end 102 and distal (or leading) end 104 of seal anchor member 100. Positioning members 114 may be composed of any suitable biocompatible material that is at least semi-resilient such that positioning members 114 may be resiliently deformed and may exhibit any suitable configuration, e.g., substantially annular or oval.

Prior to the insertion of seal anchor member 100, positioning members 114 are deformed in conjunction with the respective proximal and distal ends 102, 104 of seal anchor member 100 to facilitate the advancement thereof through tissue tract 12. Subsequent to the insertion of seal anchor member 100 within tissue tract 12, the resilient nature of positioning members 114 allows positioning members to return to their normal, substantially annular configuration, thereby aiding in the expansion of either or both of the respective proximal and distal ends 102, 104 and facilitating the transition of seal anchor member 100 from its compressed condition to its expanded condition.

Prior to the insertion of seal anchor member 100 within tissue tract 12, seal anchor member 100 is in its expanded condition in which the dimensions thereof prohibit the insertion of seal anchor member 100 into tissue tract 12. To facilitate insertion, the clinician transitions seal anchor member 100 into the compressed condition by applying a force thereto, e.g., by squeezing seal anchor member 100. Subsequent to its insertion, distal end 104, positioning member 114 and at least a section 112 of intermediate portion 106 are disposed beneath the tissue "T." Seal anchor member 100 is caused to transition from the compressed condition to the expanded condition by removing the force applied therefrom.

After successfully anchoring seal anchor member 100 within the patient's tissue "T," one or more surgical instruments 150, 160, 170 may be inserted through ports 108. FIG. 2 illustrates surgical instruments 150, 160, 170 introduced through ports 108.

In this exemplary embodiment, a trocar or cannula 150 is inserted through one port 108. The distal end 154 of the body 152 of the cannula 150 exits the distal end 104 of the surgical apparatus 10. Moreover, another port 108 is configured to receive a first surgical instrument 160 and an additional port 108 is configured to receive a second surgical instrument 170. The first surgical instrument 160 includes a tubular member 162. A distal end 164 of the tubular member 162 includes a first imaging unit 166 and a first sensing unit 168. The first imaging unit 166 may be a camera. The second surgical instrument 170 includes a tubular member 172. A distal end 174 of the tubular member 172 includes a second imaging unit 176 and a second sensing unit 178. The second imaging unit 176 may be a camera. The first and second sensing units 168, 178 may automatically detect each others presence and orientation within a body cavity. As such, the second imaging unit 176 may be tracked based on the location or orientation of the first imaging unit 166. The first imaging unit 166 may capture images of an object 190. The second imaging unit 176 may capture images of an object 180.

The first and second sensing units 168, 178 may be position sensors. One of more position sensors may be disposed in operable communication with a controller configured to receive the one or more sensor signals and to determine when one or more instruments are located within the body cavity of a patient. The position sensor may be a potentiometer, a proximity sensor (e.g., optical and/or ferromagnetic), a linear variable displacement transducer, a shaft encoder, a Hall-effect sensor and the like. The first and second sensing units 168, 178 may be configured to automatically switch the views between the main screen and the PIP screen when determining that other instruments are positioned within a body cavity.

Additionally, the first and second surgical instruments 160, 170 may communicate with a display unit 140 having a screen 142. The communication may be a wired or wireless communication. The display unit 140 may include a computer type display device using any suitable apparatus such as a cathode-ray kinescope tube, a plasma display, liquid crystal display, and so forth, or it may or may not include a device for rendering an image and may include a memory device or part of the memory device for storing an image for further processing, or for viewing, or evaluation, as may be convenient, or it may utilize a connection or coupling including such as are noted above in relation to the first and second imaging units 166, 176. The display unit 140 may be a touchscreen display unit configured to include a set of virtual icons, as discussed below with reference to FIG. 8.

It is contemplated that one skilled in the art may use the system of FIG. 1 in any procedure employing multiple endoscopes even if an access port is not used.

Figure 3A:
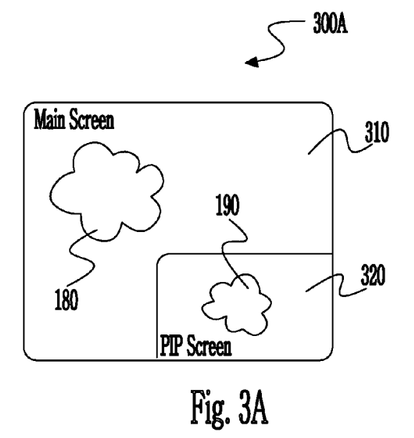
FIGS. 3A-3B are views of the display screen illustrating a picture-in-picture (PIP) configuration, where the PIP screens are smaller in size compared to the main screen, in accordance with the present disclosure.
Figure 3B:
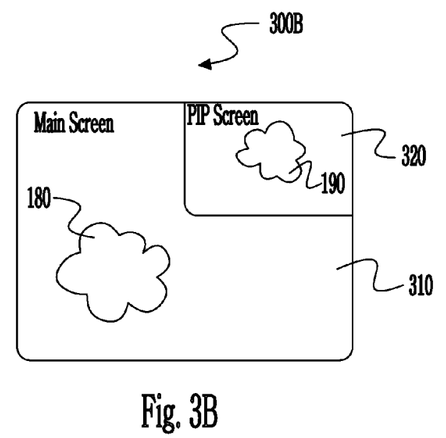

With reference to FIGS. 3A-3B, perspective views of the display screens 300A, 300B illustrating picture-in-picture (PIP) configurations are presented, where the PIP screen 320 is smaller than the main screen 310, in accordance with the present disclosure.

FIGS. 3A-3B illustrate using a picture-in-picture image or display region in accordance with an embodiment of the present disclosure. The display screen 300A includes a first display panel 310 and a second display panel 320. The first display panel 310 may be the main screen or primary screen. The second display panel 320 may be the picture-in-picture (PIP) screen or secondary screen. In general, a PIP screen typically overlays a portion of a primary screen. The main screen 310 may display an image 180 captured by the second camera 176 of the surgical instrument 170 (see FIG. 2). The PIP screen 320 may display an image 190 captured by the second camera 166 of the second surgical instrument 160 (see FIG. 2). In FIG. 3A, the PIP screen 320 is positioned at the bottom right-hand corner of the display screen 300A. In FIG. 3B, the PIP screen 320 is positioned at the top right-hand corner of the screen 300B. One skilled in the art may contemplate the PIP screen 320 positioned at any location on the screens 300A, 300B.

Figure 4:
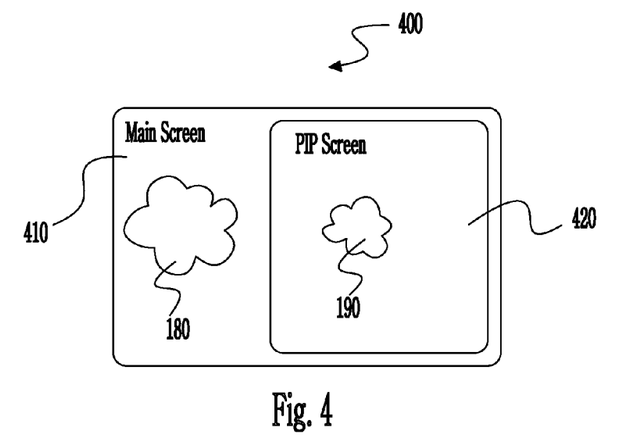
FIG. 4 is a view of the display screen illustrating a picture-in-picture (PIP) configuration, where the PIP screen is of substantially equal size to the main screen, in accordance with the present disclosure.

With reference to FIG. 4, a perspective view of the display screen 400 illustrating a picture-in-picture (PIP) configuration is presented, where the PIP screen 420 is substantially equal to the main screen 410, in accordance with the present disclosure.

FIG. 4 illustrates using a picture-in-picture image or display region in accordance with an embodiment of the present disclosure. The display screen 400 includes a first display panel 410 and a second display panel 420. The first display panel 410 may be the main screen or primary screen. The second display panel 420 may be the picture-in-picture (PIP) screen or secondary screen. The main screen 410 may display an image 180 captured by the first camera 176 of the surgical instrument 170 (see FIG. 2). The PIP screen 420 may display an image 190 captured by the second camera 166 of the second surgical instrument 160 (see FIG. 2). As shown in FIG. 4, the main screen 410 is approximately the same size as the PIP screen 420. One skilled in the art may contemplate the PIP screen 420 to be any desirable size with respect to the size of the main screen 410.

Figure 5A:
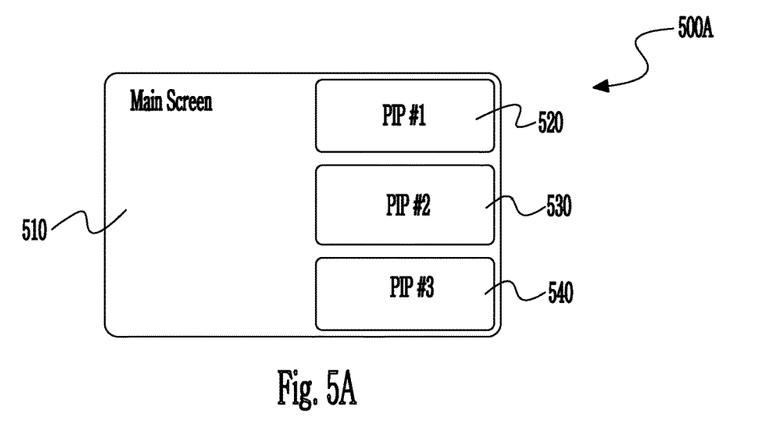
FIGS. 5A-5B are views of the display screen illustrating a picture-in-picture (PIP) configuration, where multiple PIP screens are presented to the user, either on the left side or the right side of the main screen, in accordance with the present disclosure.
Figure 5B:
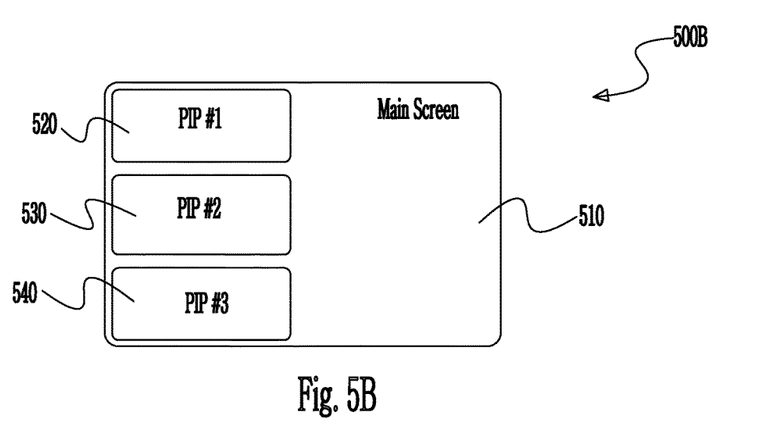

With reference to FIGS. 5A-5B, perspective views of the display screens 500A, 500B illustrating picture-in-picture (PIP) configurations is presented, where multiple PIP screens 520, 530, 540 are presented to the user, in accordance with the present disclosure.

FIGS. 5A-5B illustrate using a picture-in-picture image or display region in accordance with an embodiment of the present disclosure. The display screen 500A includes a first display panel 510, a second display panel 520, a third display panel 530, and a fourth display panel 540. The first display panel 510 may be the main screen or primary screen. The second, third, and fourth display panels 520, 530, 540 may be the picture-in-picture (PIP) screens or secondary screens. In FIG. 5A, the second, third, and fourth display panels 520, 530, 540 are vertically positioned on the right hand side of the screen 500A. In FIG. 5B, the second, third, and fourth display panels 520, 530, 540 are vertically positioned on the left hand side of the screen 500B. One skilled in the art may contemplate the PIP screens 520, 530, 540 on any portion of the screens 500A, 500B in a number of different configurations.

Figure 6:
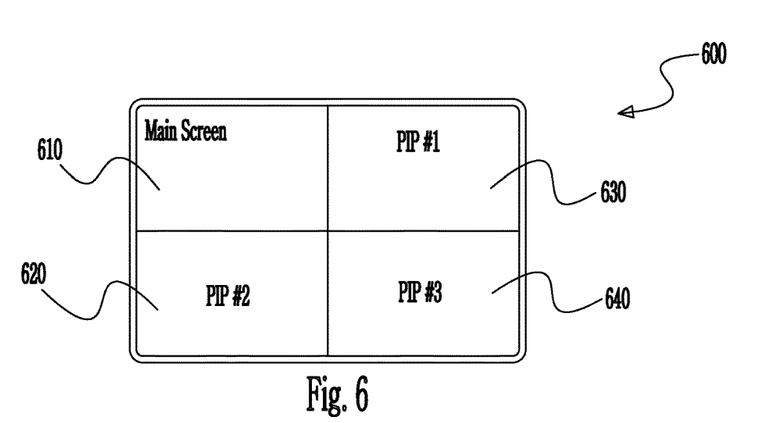
FIG. 6 is a view of the display screen illustrating a picture-in-picture (PIP) configuration, where three PIP screens are shown within a quad configuration, in accordance with the present disclosure.

With reference to FIG. 6, a perspective view of the display screen 600 illustrating a picture-in-picture (PIP) configuration is presented, where three PIP screens 620, 630, 640 are shown within a quad configuration, in accordance with the present disclosure.

FIG. 6 illustrates using a picture-in-picture image or display region in accordance with an embodiment of the present disclosure. The display screen 600 includes a first display panel 610, a second display panel 620, a third display panel 630, and a fourth display panel 640. The first display panel 610 may be the main screen or primary screen. The second, third, and fourth display panels 620, 630, 640 may be the picture-in-picture (PIP) screens or secondary screens. In FIG. 6, the display panels are displayed in a quad configuration.

Figure 7A:
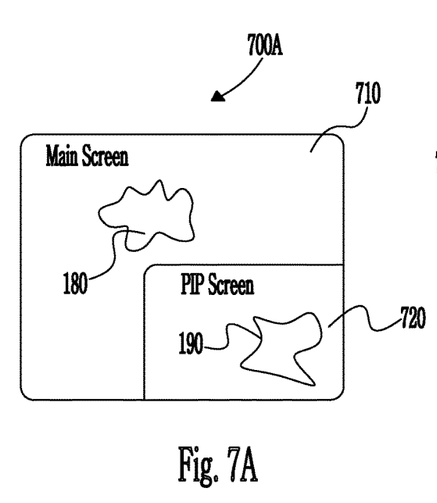
FIGS. 7A-7B are views of the display screen illustrating a picture-in-picture (PIP) configuration, where the main screen is interchanged with the PIP screen, in accordance with the present disclosure.
Figure 7B:
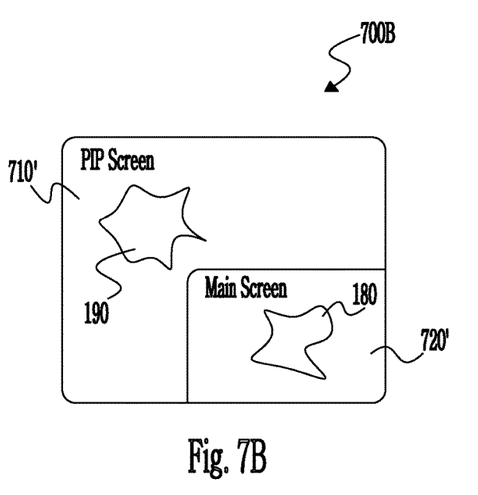

With reference to FIGS. 7A-7B, perspective views of the display screens 700A, 700B illustrating picture-in-picture (PIP) configurations is presented, where the main screen 710 is interchanged with the PIP screen 720, in accordance with the present disclosure.

FIGS. 7A-7B illustrate using a picture-in-picture image or display region in accordance with an embodiment of the present disclosure. The display screen 700A includes a first display panel 710 and a second display panel 720. The first display panel 710 may be the main screen or primary screen. The second display panel 720 may be the picture-in-picture (PIP) screen or secondary screen. The main screen 710 may display an image 180 captured by the second camera 176 of the surgical instrument 170 (see FIG. 2). The PIP screen 720 may display an image 190 captured by the first camera 166 of the second surgical instrument 160 (see FIG. 2).

In this exemplary embodiment, a function may be provided for interchanging the main screen 710 and the PIP screen 720, as shown in FIG. 7B. FIG. 7B shows the main screen interchanged with the PIP screen. In other words, the main screen 710' now illustrates the image 190 captured from the first camera 166 of the second surgical instrument 160, whereas the PIP screen 720' now illustrates the image 180 captured from the second camera 176 of the first surgical instrument 170. Therefore, a user is permitted to interchange the images displayed on the main screen and PIP screen at will. These images may also be interchanged automatically at predetermined time intervals.

Figure 8:
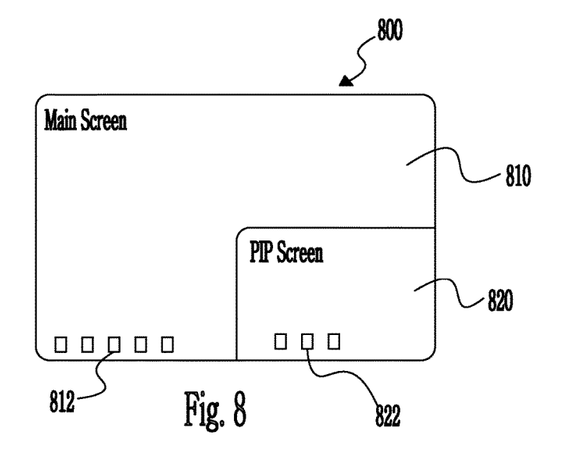
FIG. 8 is a view of the display screen including a set of virtual icons positioned on the main screen and on the PIP screen, in accordance with the present disclosure.

With reference to FIG. 8, a perspective view of the display screen 800 including sets of virtual icons 812, 822 positioned on the main screen 810 and the PIP screen 820, in accordance with the present disclosure is presented.

FIG. 8 illustrates using a picture-in-picture image or display region in accordance with an embodiment of the present disclosure. The display screen 800 includes a first display panel 810 and a second display panel 820. The first display panel 810 may be the main screen or primary screen. The second display panel 820 may be the picture-in-picture (PIP) screen or secondary screen. The first display panel 810 includes a first set of virtual buttons 812, whereas the second display panel 820 includes a second set of virtual buttons 822. The virtual buttons 812, 822 may be manipulated by a user while the surgical procedure is being performed.

In certain embodiments, the virtual buttons 812, 822 may include mode selectors, which allow the user to select one of a plurality of alternate modes, and thereby switch between different control panels corresponding to the different modes. For example, the different modes may include quad image (FIG. 6), triple PIP image (FIGS. 5A-5B), dual image (FIG. 4), or various picture-in-picture images (FIGS. 3A-3B). Additionally, the virtual buttons 812, 822 may be at least panning control icons, zooming control icons, rotating control icons, and freeze control icons. Moreover, the virtual buttons 812, 822 may also include a lighting icon for separately controlling at least intensity and color of the images captured by the imaging units 166, 176 of the first and second surgical instruments 160, 170.

Figure 9A:
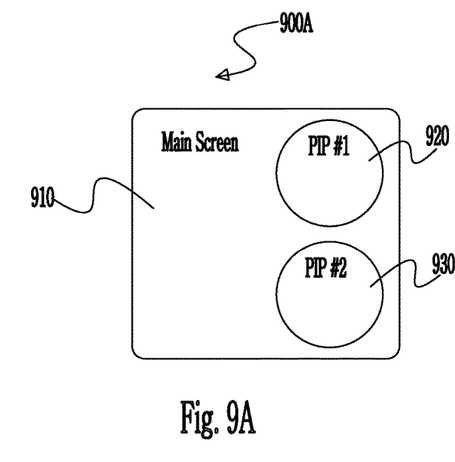
FIGS. 9A-9C are views of the display screen illustrating a picture-in-picture (PIP) configuration, where the PIP screens are readily movable, in real-time, from one position to another on the display screen, in accordance with the present disclosure.
Figure 9B:
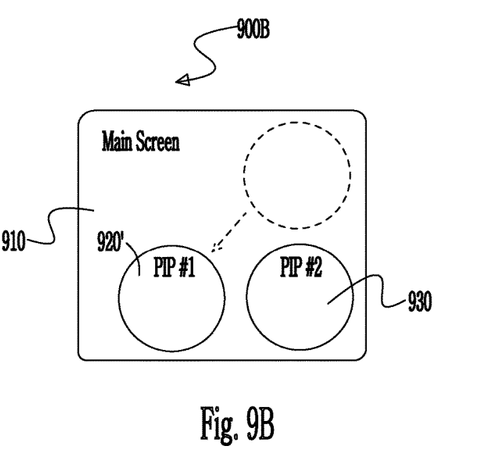
Figure 9C:
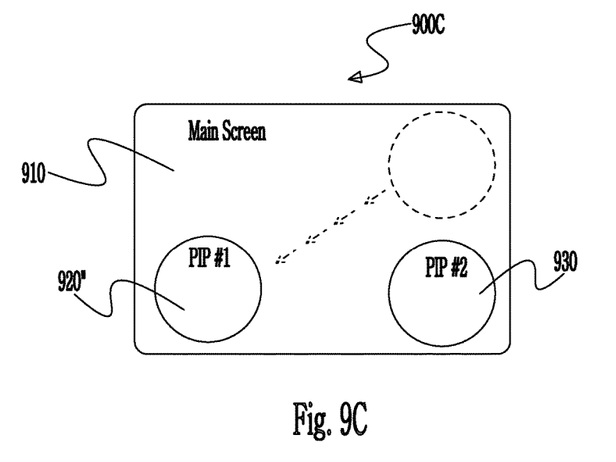

With reference to FIGS. 9A-9C, perspective views of the display screens 900A, 900B, 900C illustrating picture-in-picture (PIP) configurations is presented, where the PIP screens 920, 930 are readily movable from one position to another on the display screens 900A, 900B, 900C, in accordance with the present disclosure.

In FIG. 9A, the display screen 900A includes a first display panel 910, a second display panel 920, and a third display panel 930. The first display panel 910 may be the main screen or primary screen. The second and third display panels 920, 930 may be the picture-in-picture (PIP) screens or secondary screens. The PIP screens 920, 930 are shown as a circular shape. One skilled in the art may contemplate designing the PIP screens 920, 930 in any desirable shape.

In FIG. 9B, the display screen 900B depicts the second PIP screen 920 re-positioned from the top portion to the bottom portion of the main screen 910 and directly next to the second PIP screen 930, shown as PIP screen 920'. In FIG. 9C, the display screen 900C depicts the second PIP screen 920 re-positioned from the top portion to the bottom portion of the main screen 910 and opposite to the second PIP screen 930, as PIP screen 920". In other words, either the first PIP screen 920 or the second PIP screen 930 are permitted to be re-positioned by the user to any other positions of the displays 900A, 900B, 900C. One skilled in the art may contemplate several different repositioning methodologies.

Figure 10A:
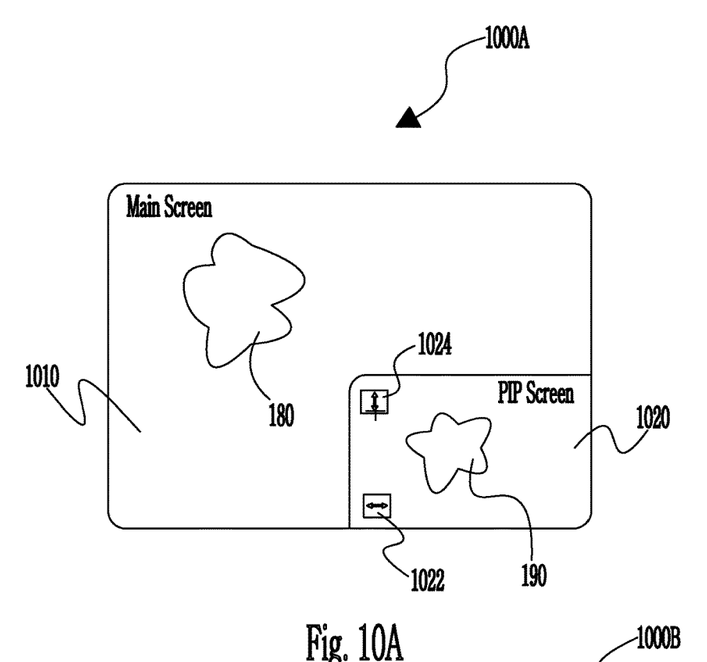
FIGS. 10A-10B are views of the display screen illustrating a picture-in-picture (PIP) configuration, where the PIP screen includes horizontal and vertical processing functions displayed thereon, in accordance with the present disclosure.
Figure 10B:
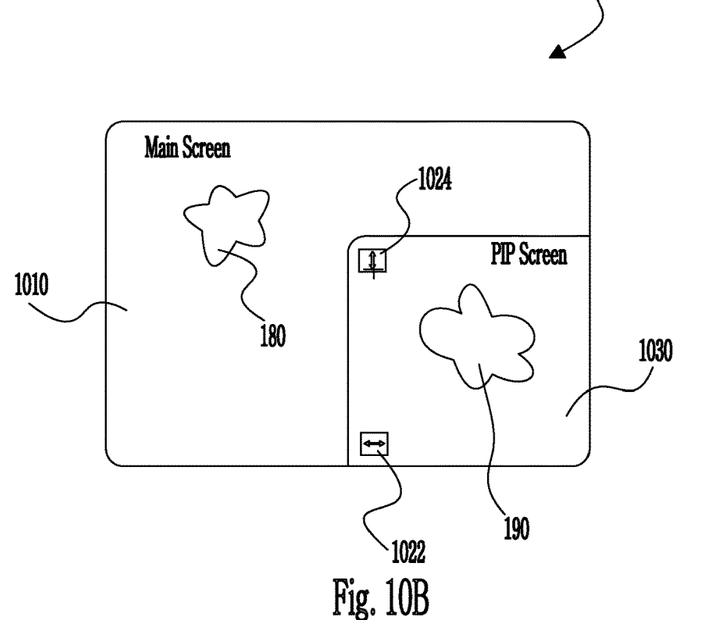

With reference to FIGS. 10A-10B, perspective views of the display screens 1000A, 1000B illustrating picture-in-picture (PIP) configurations is presented, where the PIP screen 1020 includes horizontal and vertical processing functions 1022, 1024 displayed thereon, in accordance with the present disclosure.

FIGS. 10A-10B illustrate using a picture-in-picture image or display region in accordance with an embodiment of the present disclosure. The display screen 1000A includes a first display panel 1010 and a second display panel 1020. The first display panel 1010 may be the main screen or primary screen. The second display panel 1020 may be the picture-in-picture (PIP) screen or secondary screen. The main screen 1010 may display an image 180 captured by the second camera 176 of the surgical instrument 170 (see FIG. 2). The PIP screen 1020 may display an image 190 captured by the first camera 166 of the second surgical instrument 160 (see FIG. 2).

The second display panel 1020 includes a horizontal adjustment button 1022 and a vertical adjustment button 1024. In use, a user may manipulate the horizontal adjustment button 1022 and the vertical adjustment button 1024 while a surgical procedure is being performed, in order to, for example, increase the PIP screen 1020 (display screen 1000A) to PIP screen 1030 (display screen 1000B) so that the user may get a better view of the image 190.

Therefore, with reference to FIGS. 3A-10B, several methods may be employed to aid in the transition or transitions from one or more main screens to one or more PIP screens. For example, when a secondary image is called up, the secondary image may appear to grow from the instrument location on the other screen and expand to its PIP location and size or to the full image depending on the mode selected. Alternatively, when a secondary image is called up, the secondary image may appear to grow from a seemingly off-screen location by either passing through its location on the other image or not. Alternatively, when a secondary image is called up, the secondary image may appear to grow from an icon either passing through its location on the other image or not. Alternatively, when a secondary image is called up, the secondary image may appear to grow from a fixed vanishing point either passing through its location on the other image or not.

Additionally, with reference to FIGS. 3A-10B, several more methods may be employed to aid in the transition or transitions from one or more main screens to one or more PIP screens. For example, when an image is called upon to be reduced in size, it may shrink down to its PIP location and size either by passing through its location on the other image or not. Alternatively, when an image is called upon to be reduced in size, it may shrink down to a vanishing point, either passing through its location on the other image or not. Alternatively, when an image is called upon to be reduced in size, it may shrink down to an icon either passing through its location on the other image or not. Alternatively, when an image is called upon to be reduced in size, it may shrink down to a seemingly off-screen location either passing through its location on the other image or not.

Thus, in certain embodiments, as discussed above with reference to FIGS. 3A-10B, the display panels may include one or more size icons for changing the size of the smaller section, and in some embodiments, the display panels may include one or more position icons for changing the location of the smaller section within the larger section. Additionally, in some implementations, the PIP displays may be shown side-by-side, underneath or above the primary screen, thus avoiding a portion of the primary screen being occluded. Thus, the size and position of the images or objects may be adjusted in real-time, while a surgical procedure is being performed in order to provide improved endoscopic viewing and orientation capabilities.

Moreover, even though two cameras have been described herein, it is contemplated that a plurality of cameras may be used, each capturing images for a separate and distinct PIP screen. The examples above limit themselves to two cameras for ease of illustration. Additionally, the images captured by each of the plurality of cameras may appear on demand or automatically. The images of the main screen and PIP screens may also be interchanged on demand or automatically.

Figure 11A:
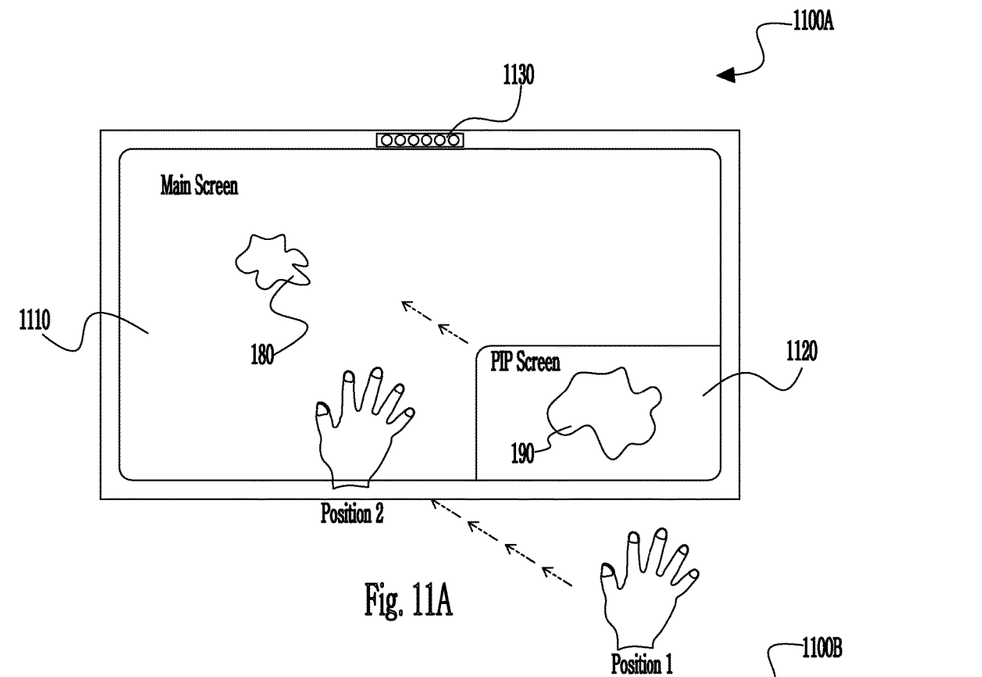
FIGS. 11A-11B are views of the display screen illustrating a picture-in-picture (PIP) configuration, the display including a motion detection unit for adjusting the size and position of the display screen via finger or hand motion commands, in accordance with the present disclosure.
Figure 11B:
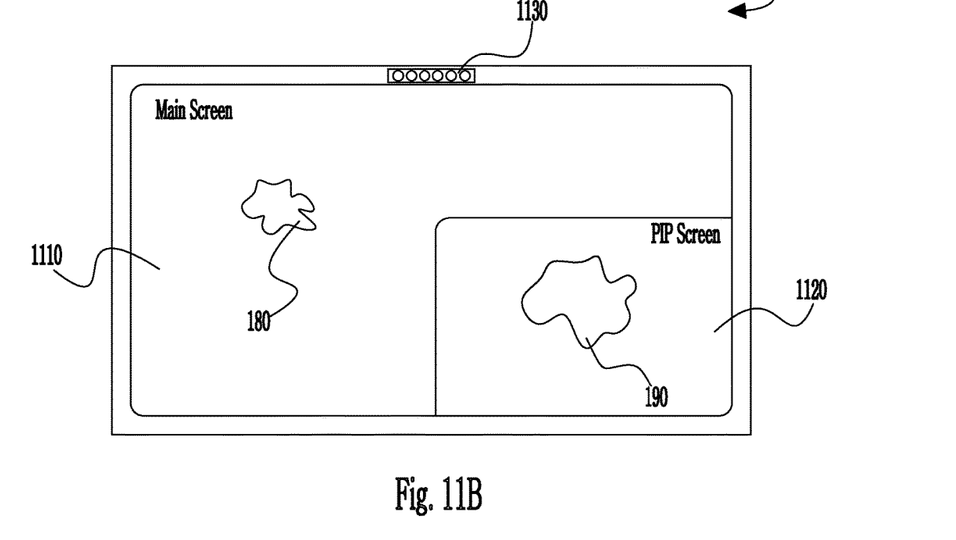

With reference to FIGS. 11A-11B, perspective views of the display screens 1100A, 1100B illustrating picture-in-picture (PIP) configurations is presented, the displays 1100A, 1100B including a motion detection unit 1130 for adjusting the size and position of the display screens 1100A, 1100B via finger or hand motion commands, in accordance with the present disclosure.

The display screen 1100A includes a first display panel 1110 and a second display panel 1120. The first display panel 1110 may be the main screen or primary screen. The second display panel 1120 may be the picture-in-picture (PIP) screen or secondary screen. The main screen 1110 may display an image 180 captured by the second camera 176 of the surgical instrument 170 (see FIG. 2). The PIP screen 1120 may display an image 190 captured by the first camera 166 of the second surgical instrument 160 (see FIG. 2).

As shown in FIG. 11A, a user may perform a hand or finger gesture in order to increase the size of the PIP screen 1120 to a bigger size 1140, as shown in FIG. 11B. For example, a user's hand may be placed at a first position in front of PIP screen 1120. The user may then move his hand toward the middle of the main screen 1110. This motion may be sensed by the motion sensor 1130 positioned on the display screens 1100A, 1100B. As such, the user may increase the size of the PIP screen by motion control via his hand or fingers. Thus, the display screens 1100A, 1100B include a motion detection unit 1130 so that a size and position of the first and second panels 1110, 1120 is adjusted based on a user's hand or finger command motions detected by the motion detection unit 1130. Thus, in this exemplary embodiment, the user need not touch the display screen but merely "motion" to adjust the size and position of the PIP screen or screens displayed over the main screen.

The use of the word "exemplary" in this disclosure is intended to mean that the embodiment or element so described serves as an example, instance, or illustration, and is not necessarily to be construed as preferred or advantageous over other embodiments or elements. The term "PIP display" has been used herein for the purposes of describing and enabling the present disclosure. However, other terms are known in the art which may be used interchangeably with "PIP display" such as "PIP picture," "PIP window," "PIP section," "PIP," "picture-on-picture," or other like terms. Similarly, although the term "primary display" has been used herein, other terms may be used in place of this term such as "main display," "main window," or the like.

Further, the terms "first display area or first display panel" and "second display area or second display panel" may be used in place of, or interchangeably with, the terms "primary display" and "PIP display." The PIP scheme may further include the software, routines and drivers used to implement the auto PIP feature. Various embodiments have been described in terms of the PIP display being launched "automatically." By "automatically" it is meant that the PIP is launched without requiring user intervention in response to an external trigger event.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A system for controlling a display of image data, the system comprising:
   a first imaging unit for capturing a first set of images, the first imaging unit including a first sensing unit;
   a second imaging unit for capturing a second set of images, the second imaging unit including a second sensing unit, wherein the first sensing unit automatically detects the presence and orientation of the second sensing unit and the second sensing unit automatically detects the presence and orientation of the first sensing unit; and
   a display unit configured to display the image data in a picture-in-picture mode, such that the display unit displays the first set of images in a first panel and the second set of images in a second panel, wherein the second set of images appears to originate from a location of the second sensing unit in the first set of images on the first panel when the second set of images are called up to visually aid a user of the system when transitioning from viewing the first set of images on the first panel to viewing the second set of images on the second panel.

2. The system according to claim 1, wherein the display unit is a touchscreen display unit configured to include a set of virtual icons including panning control icons, zooming control icons, rotating control icons, and freeze control icons.

3. The system according to claim 1, wherein the display unit includes a storage medium for storing the first and second set of images captured by the first and second imaging units.

4. The system according to claim 1, wherein the picture-in-picture mode allows for at least a dual image panel, a triple image panel, and a quad image panel.

5. The system according to claim 1, wherein a size of the first set of images and a size of the second set of images is permitted to be adjusted in real-time.

6. The system according to claim 1, wherein a position of the first set of images and a position of the second set of images is permitted to be adjusted in real-time.

7. The system according to claim 1, wherein each of the first and second panels includes a lighting icon for separately controlling at least intensity and color of the first and second set of images captured.

8. The system according to claim 1, wherein the first panel is selectively interchanged with the second panel, and vice versa.

9. The system according to claim 1, wherein each of the first and second panels include a horizontal and vertical processing function for selectively performing horizontal and vertical enlargement or reduction of the first and second set of images captured.

10. The system according to claim 1, wherein the display unit includes a motion detection unit so that a size and position of the first and second panels is adjusted based on a user's hand or finger command motions detected by the motion detection unit.

11. A surgical system for displaying image data, comprising:
    a support structure including a plurality of ports for facilitating introduction of a plurality of surgical instruments therethrough;
    a plurality of imaging units mounted on the plurality of surgical instruments for capturing a plurality of images, each imaging unit of the plurality of imagining units including a sensing unit, wherein each sensing unit automatically detects the presence and orientation of the other sensing units; and
    a display unit for displaying one or more picture-in-picture configurations of the plurality of images captured by the plurality of imaging units, the picture-in-picture configurations configured to display the plurality of images within a plurality of panels, wherein a first set of images from a first imaging unit of the plurality of imaging units appears to originate from a location of a first sensing unit of the first imagining unit in a second set of images from a second imaging unit of the plurality of imaging units when the first set of images are called up to visually aid a user of the system when transitioning from viewing the second set of images to viewing the first set of images.

12. The surgical system according to claim 11, wherein the display unit includes a storage medium for storing the plurality of images captured by the plurality of imaging units.

13. The surgical system according to claim 11, wherein the display unit is divided into a plurality of sections for separately displaying the image data supplied by a corresponding plurality of imaging units.

14. The surgical system according to claim 11, wherein at least a size and a position of the plurality of images is permitted to be adjusted in real-time.

15. The surgical system according to claim 11, wherein the plurality of panels are selectively interchanged with each other.

16. The surgical system according to claim 11, wherein each of the plurality of panels includes a horizontal and vertical processing function for selectively performing horizontal and vertical enlargement or reduction of the plurality of images captured.

17. The surgical system according to claim 11, wherein the display unit includes a motion detection unit so that a size and a position of the plurality of panels is adjusted based on a user's hand or finger command motions detected by the motion detection unit.

18. A method of displaying image data, the method comprising:

capturing a first set of images via a first imaging unit, the first imaging unit including a first sensing unit;
capturing a second set of images via a second imaging unit;
the second imaging unit including a second sensing unit, wherein the first sensing unit automatically detects the presence and orientation of the second sensing unit and the second sensing unit automatically detects the presence and orientation of the first sensing unit;
displaying the image data in a picture-in-picture mode, via a display unit configured to display the first set of images in a first panel having a first size and the second set of images in a second panel having a second size, wherein the second set of images appears to originate from a location of the second imaging unit in the first set of images on the first panel when the second set of images are called up to visually aid a user of the system when transitioning from viewing the first set of images on the first panel to viewing the second set of images on the second panel.

* * * * *